(12) United States Patent
West et al.

(10) Patent No.: US 7,972,374 B2
(45) Date of Patent: Jul. 5, 2011

(54) SECURING RODS AND MODULAR GRAFT SYSTEMS

(75) Inventors: Karl J. West, Geneva, OH (US); Roy K. Greenberg, Bratenahl, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 45 days.

(21) Appl. No.: 12/260,460

(22) Filed: Oct. 29, 2008

(65) Prior Publication Data

US 2009/0138068 A1   May 28, 2009

Related U.S. Application Data

(60) Provisional application No. 61/000,782, filed on Oct. 29, 2007.

(51) Int. Cl.
*A61F 2/06* (2006.01)
(52) U.S. Cl. ............... 623/1.16; 623/1.13; 623/1.15
(58) Field of Classification Search ........ 623/1.12–1.13, 623/1.35, 1.15, 1.16; 606/157
See application file for complete search history.

(56) References Cited

U.S. PATENT DOCUMENTS

| 3,435,823 | A | 4/1969 | Edwards | |
|---|---|---|---|---|
| 5,575,817 | A | 11/1996 | Martin | 623/1 |
| 5,800,526 | A | 9/1998 | Anderson et al. | 623/1 |
| 5,824,037 | A | 10/1998 | Fogarty et al. | 623/1 |
| 6,035,856 | A | 3/2000 | LaFontaine et al. | 128/898 |
| 6,110,198 | A * | 8/2000 | Fogarty et al. | 623/1.12 |
| 6,193,745 | B1 | 2/2001 | Fogarty et al. | 623/1.12 |
| 6,231,581 | B1 * | 5/2001 | Shank et al. | 606/157 |
| 6,361,556 | B1 | 3/2002 | Chuter | 623/1.11 |
| 6,773,454 | B2 | 8/2004 | Wholey et al. | 623/1.15 |
| 6,896,688 | B2 | 5/2005 | Richard et al. | 606/153 |
| 6,986,786 | B1 | 1/2006 | Smith | 623/1.36 |
| 7,232,459 | B2 * | 6/2007 | Greenberg et al. | 623/1.13 |
| 2006/0085060 | A1 | 4/2006 | Campbell | 623/1.26 |
| 2007/0038288 | A1 | 2/2007 | Lye et al. | 623/1.16 |

* cited by examiner

*Primary Examiner* — David Isabella
*Assistant Examiner* — Seema Swaminathan
(74) *Attorney, Agent, or Firm* — Brinks Hofer Gilson & Lione

(57) ABSTRACT

Modular graft systems with conjoinable grafts comprising graft material with the system comprising a first and second graft prosthesis with mating ends, securing rods attached to one of the mating ends comprising at least one spike that juts from the securing rod. The other of the mating ends is double layered with graft material for receiving at least one spike in the first layer of graft material when the mating ends are conjoined.

15 Claims, 3 Drawing Sheets

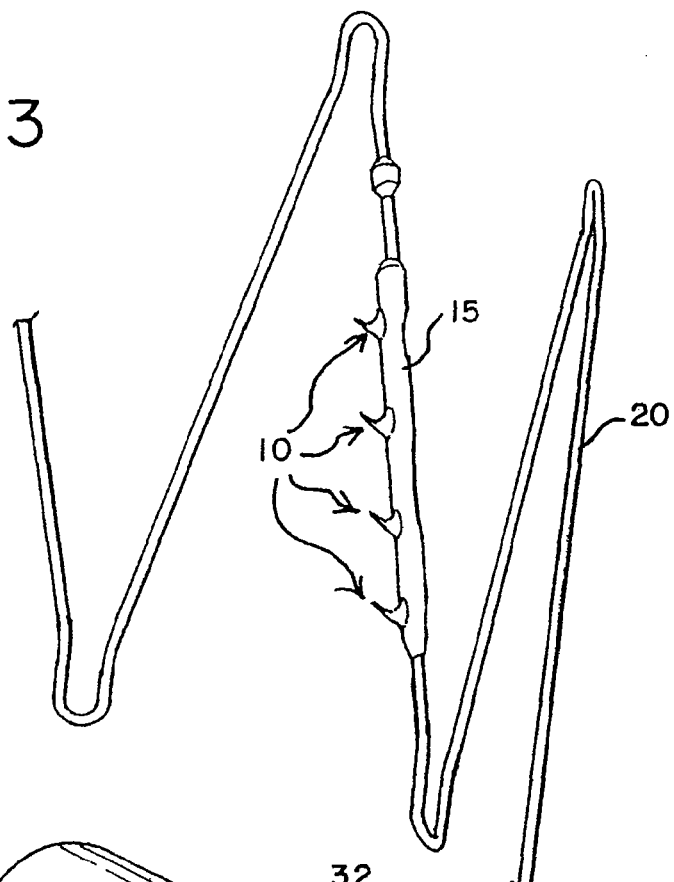
FIGURE 3
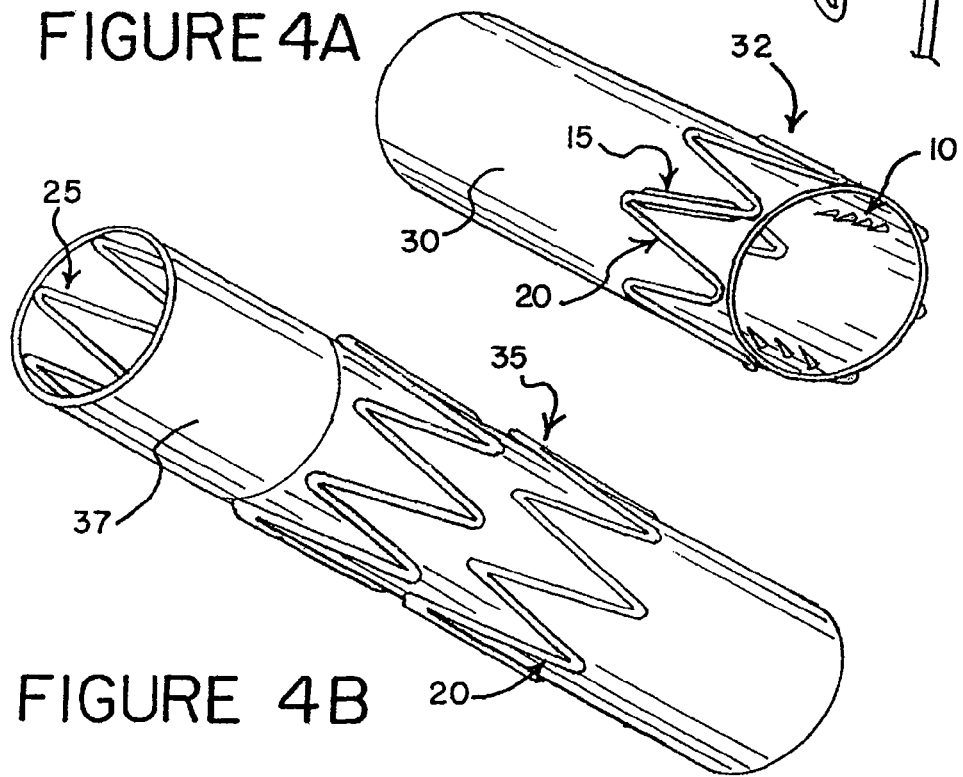
FIGURE 4A
FIGURE 4B

SECURING RODS AND MODULAR GRAFT SYSTEMS

CROSS-REFERENCE TO RELATED APPLICATION

This application claims the benefit of U.S. Provisional Application No. 61/000,782, filed Oct. 29, 2007, which is incorporated herein by reference in its entirety.

TECHNICAL FIELD

This invention relates to modular graft systems with improved mating apparatuses.

BACKGROUND

Endovascular stent grafts are increasingly used to treat aneurysms in the human aorta. As a result, stent grafts are being mated with one another in the aorta. When endovascular stent grafts are joined together in vascular surgery, exsanguination may occur at the interface between the grafts if the modular joints separate. Over time, some modular joints may degenerate and slip, predisposing the aneurysm to a risk of pressurization, rupture, and potential exsanguination. Exsanguination must be minimized to decrease the formation of blood clots and the amount of time the vessel is deprived of blood. A tight seal between the interconnected grafts helps minimize exsanguinations.

Current methods of mating endovascular stent grafts involve installing one device interior to a second device. The overlap area, also known as the seal zone, is facilitated by direct material-to-material contact; that is, the interior mated device (male) has a stent on its interior and the exterior mated device (female) has a stent on its exterior.

This configuration places material against material to gain the greatest surface area of contact as well as taking advantage of the forces of friction between the two fabrics. Current methods for mating devices in the aorta need revision. If devices mated using current methods ever separated, it could lead to device system failure with the repressurization of the aortic aneurysm.

The problem of device disunion has to be addressed, preferably with devices with strengthened mating zones. There is a need in the art to increase force resistance in the seal zones to provide a longer lifespan for the modular endovascular systems.

BRIEF SUMMARY

One aspect of the present invention provides a modular graft system of conjoinable grafts comprising graft material with the system comprising a first graft prosthesis with a mating end and a second graft prosthesis with a mating end. A securing rod is attached to the mating end of the first graft prosthesis and the securing rod comprises at least one spike that juts from the securing rod. The at least one spike is received by a first layer of graft material on the mating end of the second graft prosthesis upon conjoining the mating ends of the first and the second graft prosthesis. The rods can be attached to the stent struts or graft material to be oriented against a predetermined dislocation force.

In yet another aspect, there is a method of implanting a modular graft system that comprises a first graft prosthesis having a mating end, a second graft prosthesis having a mating end, and the mating ends overlapping one another. The method comprises providing a securing rod attachable to the mating end of the first graft prosthesis, the securing rod comprising at least one spike jutting from the securing rod; attaching the securing rod to one of the mating ends; and securing the first and second graft prosthesis together by conjoining the mating ends of both endovascular grafts such that the at least one spike is received by the mating end of the opposing endovascular graft.

BRIEF DESCRIPTION OF THE DRAWINGS

FIG. 3 illustrates a stent strut with a securing rod attached.

FIG. 4A illustrates an embodiment where the mating end of the first graft prosthesis has spikes on securing rods pointing toward the lumen of the mating end and is designed to receive the mating end of the second graft prosthesis illustrated in FIG. 4B.

DETAILED DESCRIPTION OF THE DRAWINGS AND THE PREFERRED EMBODIMENTS

Figure 1:
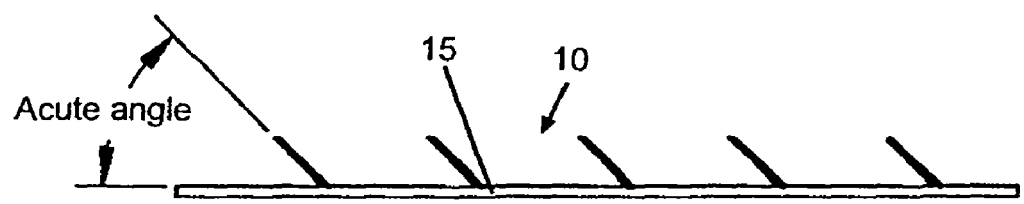
FIG. 1 is a profile view of a securing rod with five spikes.

Unless defined otherwise, all technical and scientific terms used herein have the same meaning as commonly understood to one of ordinary skill in the art to which this invention belongs.

Throughout this specification, when discussing the application of this invention to the aorta, the term distal, with respect to a prosthesis, is intended to refer to the end of the prosthesis furthest away in the direction of blood flow from the heart, and the term proximal is intended to mean the end of the prosthesis that, when implanted, would be nearest to the heart.

The term "graft or graft material" means a generally canular or tubular member which acts as an artificial vessel or prosthesis. A graft by itself or with the addition of other elements, such as structural components, can be an endoluminal prosthesis. Endoluminal prostheses are shown in FIGS. 4A, 4B, 5A, and 5B. The graft comprises a single material, a blend of materials, a weave, a laminate, or a composite of two or more materials. The graft can also comprise polymer material that aid in decreasing the incidence of delamination of the grafts used in the modular systems.

The graft material is a biocompatible material that is both flexible and abrasion resistant. Preferably, the graft material is a woven polyester. More preferably, the graft material is a polyethylene terephthalate (PET), such as DACRON® (DUPONT, Wilmington, Del.) or TWILLWEAVE MICREL® (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids.

In another embodiment, the woven graft material may be made of a single material, or it may be a blend, weave, laminate, or composite of two or more materials. The graft material may also include other additives, such as plasticizers, compatibilizers, surface modifiers, biological materials such as peptides and enzymes, and therapeutic agents such as drugs or other pharmaceutically effective medicaments. The therapeutic agents can comprise agents, or combinations thereof, that can affect the cells in a vessel wall, including drugs, chromophores, and nucleic acids. Therapeutic agents also comprise diagnostics such as radiopaque compounds that allow the vessel to be visualized by fluoroscopy or like methods. Therapeutic agents can also comprise antimicrobial agents, such as antibacterial and antiviral agents.

Biocompatible polyurethanes can be used in some embodiments of the graft material. Examples of biocompatible polyurethanes include Thoralon® (THORATEC, Pleasanton, Calif.), BIOSPAN®, BIONATE®, ELASTHANE®, PURSIL® and CARBOSIL® (POLYMER TECHNOLOGY GROUP, Berkeley, Calif.). As described in U.S. Pat. No. 6,939,377, incorporated herein by reference, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A polymer graft material can be formed from these two components by dissolving the base polymer and additive in a solvent such as dimethylacetamide (DMAC) and solidifying the mixture by solvent casting or by coagulation in a liquid that is a non-solvent for the base polymer and additive.

In addition to polyurethane ureas, other polyurethanes, preferably those having a chain extended with diols, may be used as the graft material. Polyurethanes modified with cationic, anionic, and aliphatic side chains may also be used. See, for example, U.S. Pat. No. 5,017,664, which is incorporated herein by reference. Polyurethanes may need to be dissolved in solvents such as dimethyl formamide, tetrahydrofuran, dimethyacetamide, dimethyl sulfoxide, or mixtures thereof.

The polyurethanes may also be end-capped with surface active end groups, such as, for example, polydimethylsiloxane, fluoropolymers, polyolefin, polyethylene oxide, or other suitable groups. See, for example, the surface active end groups disclosed in U.S. Pat. No. 5,589,563, which is incorporated herein by reference.

In one embodiment, the graft material may contain a polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. Examples of siloxane-polyurethanes are disclosed in U.S. Pat. Pub. No. 2002/0187288 A1, which is incorporated herein by reference.

The graft may contain polytetrafluoroethylene or ePTFE. The structure of ePTFE can be characterized as containing nodes connected by fibrils. The structure of ePTFE is disclosed, for example, in U.S. Pat. Nos. 6,547,815 B2; 5,980,799; and 3,953,566; all of which are incorporated herein by reference.

If so desired, the polymers described above can be processed to form porous polymer grafts using standard processing methods, including solvent-based processes such as casting, spraying, and dipping, and melt extrusion processes. Extractable pore forming agents can be used during processing to produce porous polymer graft material. Examples of the particulate used to form the pores include a salt, including, but not limited to, sodium chloride (NaCl), sodium bicarbonate (NaHCO$_3$), Na$_2$CO$_3$, MgCl$_2$, CaCO$_3$, calcium fluoride (CaF$_2$), magnesium sulfate (MgSO$_4$), CaCl$_2$, AgNO$_3$, or any water soluble salt. However, other suspended particulate materials may be used. These include, but are not limited to, sugars, polyvinyl alcohol, cellulose, gelatin, or polyvinyl pyrolidone. Preferably, the particulate is sodium chloride; more preferably, the particulate is a sugar.

Therapeutic agents can be incorporated into the graft material of the prosthesis, or into the biocompatible coating which encapsulates the stent, so that they can be released into the body surrounding the lumen wall upon expansion and curing of the prosthesis. Therapeutic agents or medicaments can be impregnated into the lumen wall by pressure from expansion of the prosthesis. The therapeutic agent can also be photoreleasably linked to the surface of the prosthesis so that, upon contact with the surrounding lumen wall, the agent is released onto the cells of the adjacent vascular wall by exposure to radiation delivered via an optical fiber.

The term "stent" means any device that provides rigidity, expansion force, or support to a prosthesis, such as a stent graft. In one configuration, the stent may represent a plurality of discontinuous devices. In another configuration, the stent may represent one device. The stent may be located on the exterior of the device, the interior of the device, or both. Stents may have a wide variety of configurations and may be balloon-expandable or self-expanding. Typically, stents have a circular cross-section when fully expanded, so as to conform to the generally circular cross-section of a body lumen. In one example, a stent 20 may comprise struts and acute bends or apices that are arranged in a zig-zag configuration in which the struts are set at angles to each other and are connected by the acute bends as seen in FIG. 3. The stent struts may have a thickness ranging from about 0.060 mm to about 0.20 mm and all combinations and subcombinations therein.

In some embodiments, the stent 20, the spikes 10, and the securing rod 15, as shown in FIGS. 1, 2A, 2B, and 2C, are formed from nitinol, stainless steel, tantalum, titanium, gold, platinum, inconel, iridium, silver, tungsten, cobalt, chromium, or another biocompatible metal, or alloys of any of these. Examples of other materials that may be used include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these. Preferably, the stent is a nitinol or stainless steel stent. In some embodiments, the spikes and the securing rod are formed separately from the stent.

Figure 2A:
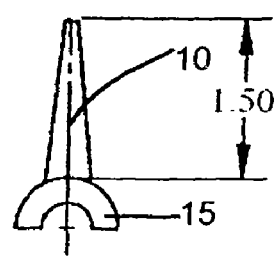
FIGS. 2A, 2B, and 2C are end views of the securing rod with protruding stents having carrying lengths.
Figure 2B:
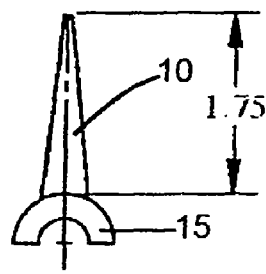
Figure 2C:
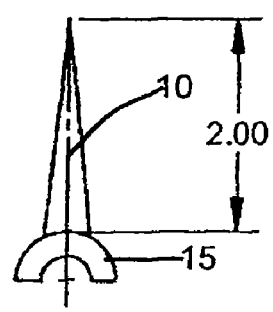

The present invention provides a securing rod 15 for conjoining endovascular grafts as shown in FIG. 1. The securing rods 15 are preferably made from stainless steel tubes or rods that are cut along the length into two halves such that the securing rod 15 conforms to a stent strut. In some embodiments the cross-section of the securing rod 15 is a part of a circle as illustrated in FIGS. 2A, 2B, and 2C. The cross-section conforms the rod 15 to the surface of a stent strut. The rod 15 can then be attached to the stent strut using methods known in the art. The cross-section can be polygonal in some embodiments.

Figure 5A:
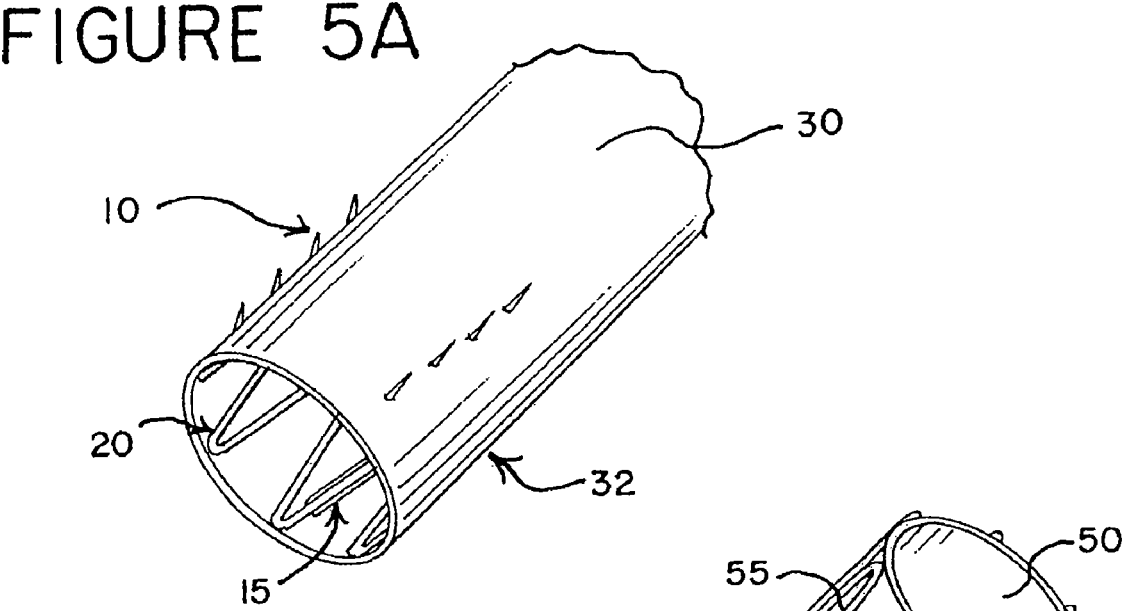
FIG. 5A depicts an embodiment where the mating end of the first graft prosthesis is designed to be received by the mating end of the second graft prosthesis illustrated in FIG. 5B.

The rod 15 in FIG. 1 comprises five spikes 10 that jut from the securing rod 15 and at a selected angle. The spikes 10 can jut from the stent struts 20 at the same selected angle or at independently selected angles. The spikes 10 in FIG. 1 are arranged at an acute angle. Depending on the position of the securing rod, the spikes 10 can jut either outwardly away from the graft lumen, as seen in FIG. 5A, or inwardly toward the graft lumen, as seen in FIG. 4A. The spikes 10 also can be oriented such that the tips are pointing in a distal direction to discourage downward (or distal) migration. The spikes 10 also can be oriented such that the tips are pointing in a proximal direction to discourage upward (or proximal) migration. This latter arrangement can be seen in FIG. 5A. The spikes are oriented against a predetermined dislocation force. For instance, the spikes 10 in FIG. 5A are oriented in a proximal direction to discourage the distal migration of the second graft prosthesis 35 in FIG. 5B when the graft 35 is mated with the first graft prosthesis 30.

The spikes 10 on the securing rods 15 resemble thorns on a rose. The spikes 10 can be laser cut from the rods 15 such that they are integrated with the stent strut 20. The spikes 10 can be attached to the securing rod 15 using other methods known in the art. Although five spikes 10 are shown in FIG. 1, there are embodiments with at least one spike, two spikes, or three spikes attached to the securing rods.

The securing rod 15 also can be attached to a stent strut 10 by soldering or the like prior to suturing to the fabric. The securing rod 15 is attached to a stent strut 10 by soldering in FIG. 3. The securing rods 15 preferably are attached to the mating end of an endovascular graft and, preferably, in the overlap area between the first and second graft prosthesis. In some embodiments, the securing rods 15 can be attached to both the first and second graft prosthesis in a modular graft system.

The present invention addresses the problem of device disunion by providing a modular graft system of conjoinable grafts comprising graft material. The system comprises a first graft prosthesis 30 with a mating end 32 and a second graft prosthesis 35 with a mating end 37. A securing rod 15 is attached to the mating end 32 of the first graft prosthesis 30, the securing rod 15 comprising at least one spike 10 jutting from the securing rod 15. The first graft prosthesis 30 can comprise more than one securing rod 15. The at least one spike 10 on the securing rod 15 is received by a first layer 40 of graft material of the mating end 37 of the second graft prosthesis 35 upon conjoining the mating ends 32, 37 of the first and the second graft prostheses 30, 35.

A profile of a securing rod 15 with spikes 10 can be seen in the mechanical drawing in FIG. 1. FIGS. 2A, 2B, and 2C are terminal views of the spike array with varying spike lengths, for instance: 1.50 mm, 1.75 mm, and 2.00 mm. The spikes 10 are oriented on the graft such that they point in a proximal direction as shown in FIG. 4A where the second graft prosthesis 35 would be implanted into the mating end 32 of the first graft prosthesis 30.

There are embodiments where the first graft prosthesis 30 has a mating end 32 that receives mating end 37 of a second graft prosthesis 35. The first graft prosthesis comprises a lumen therethrough and at least one spike 10 that juts toward the lumen of the mating end 32 of the first graft prosthesis 30. As illustrated in FIG. 4A, the mating end 32 of the first graft prosthesis 30 is at the distal portion of the graft. The securing rods 15 are attached to the external stent and protrude through the fabric of the first graft prosthesis 30. The spikes 10 have sufficient length to penetrate through a layer of graft material and still have enough length to grab the fabric of the second graft prosthesis 35. The securing rods 15 also can be attached to interior stent struts on mating end 32 of the first graft prosthesis 30. There the spikes 10 do not penetrate the graft material of the first graft prosthesis 30. The second graft prosthesis 35, or male device, receives the spikes 10 when mated with the first graft prosthesis 30, or female device. The spikes 10 can also be attached to external stent struts and jut away from the lumen of the endovascular graft. Joining the first and second graft prosthesis in such a way increases the amount of force needed to pull the grafts apart.

Figure 5B:
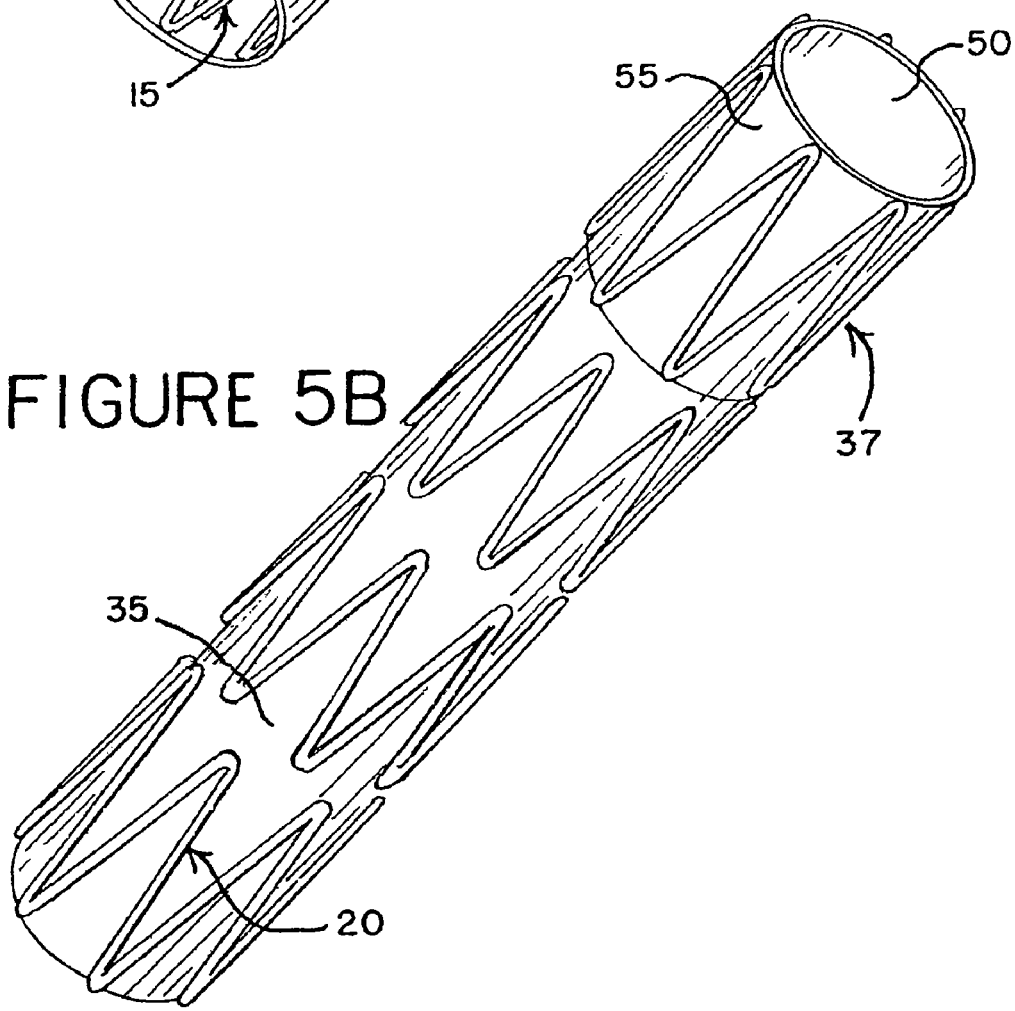

FIG. 5B shows a second graft prosthesis 35 with two layers 50, 55 on the mating end 37. The first layer 50 of graft material receives the spikes 10. The mating end 37 of the second graft prosthesis 35 further comprises a second layer 55 of graft material that provides an outer surface for the mating end 37 of the second graft prosthesis 35. The embodiment shown in FIG. 4B can also have two layers with the inner layer preventing the spikes 10 from protruding into blood flow and the outer layer that receives the spikes 10.

The fabric-to-fabric seal is maintained in the mating zone between the first and second graft prosthesis. The distal stent 20 of the first graft prosthesis 30 in FIG. 4A is on the external side of mating end 32 and the proximal stent 25 of the second graft prosthesis 35 is on the internal side of mating end 37. The graft system can further comprise a second securing rod comprising at least one spike also attached to the mating end 37 of the second graft prosthesis 35 such that the at least one spike of the second securing rod is received by the graft material of the mating end 37 of the first graft prosthesis 30 upon conjoining the two endovascular grafts. The system can further comprise more than one second securing rod attached to the mating end 37 of the second graft prosthesis 35. Another feature of the placement of the spikes on the internal side of the first graft prosthesis 30 is the prevention of sheath damage.

FIG. 5A illustrates another embodiment where the first graft prosthesis 30 comprises a lumen therethrough and the spikes 10 jut outwardly away from the lumen of the first graft prosthesis 30. The first graft prosthesis 30 is the male graft and is received by the second graft prosthesis 35. The stent struts 20 are attached to the interior side of the mating end 32 of the first graft prosthesis 30 with the spikes 10 penetrating the graft material of the first graft prosthesis 30. Although not shown the stent struts 20 can be attached to the external side of the mating end 32 of the first graft prosthesis 30 with the spikes jutting away from lumen of the prosthesis 30.

FIG. 5B depicts the second graft prosthesis 35, or female end, that receives the mating end 32 of the first graft prosthesis 30 shown in FIG. 5A. The mating end 37 of the second graft prosthesis 35 is doubled layered such that the first layer 50 receives the spikes 10 and the second layer 55 provides an outer surface for the mating end 37 of the second graft prosthesis 35.

The present invention also provides a method of implanting a modular graft system that comprises a first graft prosthesis 30 having a mating end 32 and a second graft prosthesis 35 having a mating end 37. The mating ends 32, 37 preferably overlap one another. The method comprises providing a securing rod 15 attachable to the mating end 32 of the first graft prosthesis 30 or the mating end 37 of the second graft prosthesis 35. The securing rod 15 comprises at least one spike 10 jutting from the securing rod 15. The securing rod 15 is attached to one of the mating ends 32, 37. The first 30 and second 35 endovascular grafts are secured together by conjoining the mating ends 32, 37 of both endovascular grafts such that at least one spike 10 is received by the mating end of the opposing endovascular graft.

The endovascular grafts are conjoined in a male-female fashion. In FIG. 5A, the first graft prosthesis 30 acts as the male end. In such embodiments, the first graft prosthesis 30 comprises securing rods 15 with spikes 10 that jut away from the lumen of the graft. This mating end 32 is then inserted into the mating end 37 (or female end) of the second graft prosthesis 35 shown in FIG. 5B. The first layer 50 of the mating end 37 of the second graft prosthesis 35 receives the spikes 10 jutting from the securing rods 15.

FIG. 4A depicts an embodiment where the first graft prosthesis 30 acts as the female end. In such embodiments, the securing rods 15 comprise spikes 10 that jut toward the lumen of the mating end 32 of the graft. The mating end 37 of the second graft prosthesis 35, shown in FIG. 4B, is inserted into the mating end 32 of the first graft prosthesis 30.

EXAMPLES

The testing was performed using an Alliance RT/5 MTS tensile testing machine. The MTS is connected to a computer terminal that is used to control the machine, collect, and process the data. A pump in a water bath was used to internally pressurize the mated devices to 60 mmHg to simulate the radial pressure exerted by blood upon the devices when deployed in vivo.

A pressurization pump system was attached to the load cell located on the tensile arm of the MTS. This pressurization pump system was then attached to the proximal end of the proximal device that was completely immersed in the water bath. The proximal device was mated on the external face of an adapter fitting. A hose clamp was placed at the mating area of the proximal device to seal the device around the adapter fitting and to act as an anchoring system. The proximal device was mated to the distal device with a one-stent overlap.

The mating surfaces had a material-to-material interface with the stents being on the internal side of the male device and external side of the female device. The male device was loaded into a sheath that was inserted into the female device and then deployed such that the graft of the female device overlapped the proximal stent of the male device. Once the mating overlap area had been ballooned to expand the stents per manufacturer recommendation, the proximal device was fixed to the proximal arm with the hose clamp. The distal device was screw-clamped in place inside the water bath. The devices were then pressurized to 60 mmHg and the testing was performed at 0.1 mm/second increments. The test was not stopped until the devices were completely separated. This procedure was performed once for each of the spiked setups as a preliminary proof-of-concept.

All the data gathered for this protocol is presented in the table below.

| Spiked Stent Pullout | |
|---|---|
| Spikes | Force (N) |
| Short | 14.6 |
| Medium | 15.8 |
| Long | 24.9 |

The amount of force required to separate any of the three setups tested was more than unspiked mated devices. The long spike stent setup required much more force for device separation than any other test performed prior to this protocol in this lab. Post-pullout imaging shows that failure of the mated devices occurred due to the bending of the spikes in the reverse of their original orientation.

Microscopy would be required to investigate if there is any damage to the fabric. When the device mating zone was ballooned using a Cook Inc. compliant balloon, the balloon did not rupture for any of the spike lengths being tested. This would indicate that the spikes do not pass through the fabric into the blood flow of the male device as hypothesized. The spikes only grabbed the fabric without fully penetrating it. Electron microscopy has also been used to document the stability of the materials after several thousand simulated heart beats.

Throughout this specification, various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. A modular endovascular graft system of conjoinable prostheses, the system comprising:
   a first graft prosthesis with a mating end comprising a mating surface and a second graft prosthesis comprising graft material with a mating end comprising a mating surface;
   a securing rod attached to the mating end of the first graft prosthesis, the securing rod comprising at least one spike jutting from the securing rod and oriented against a predetermined dislocation force;
   wherein the at least one spike is received by a first layer of graft material on the mating end of the second graft prosthesis upon conjoining the mating ends of the first and the second graft prosthesis;
   wherein the at least one spike protrudes through the first graft prosthesis and grabs the graft material of the mating end of the second graft prosthesis without penetrating through the graft material of second prosthesis; and
   wherein the mating surfaces of the first graft prosthesis and the second graft prosthesis form a material to material interface to provide a fluid tight seal at the interface when conjoined.

2. The modular graft system of claim 1 wherein the securing rod is attached to a stent strut.

3. The modular graft system of claim 1 further comprising more than one securing rod.

4. The modular graft system of claim 1 wherein the at least one spike is laser cut from the securing rod.

5. The modular graft system of claim 1 wherein the first graft prosthesis comprises a lumen therethrough and the at least one spike juts toward the lumen of the first graft prosthesis.

6. The modular graft system of claim 1 wherein the first graft prosthesis comprises a lumen therethrough and the at least one spike juts away from the lumen of the first graft prosthesis.

7. The modular graft system of claim 1 wherein the at least one spike is laser cut from the securing rod.

8. The modular graft system of claim 1 wherein the first layer of graft material on the mating end of the second graft prosthesis receives the at least one spike.

9. The modular graft system of claim 1 wherein the mating end of the second graft prosthesis further comprises a second layer of graft material that provides an inner diameter for the second graft prosthesis.

10. The modular graft system of claim 1 wherein the mating end of the second graft prosthesis further comprises a second layer of graft material that defines an outer surface of the second graft prosthesis when conjoined.

11. The modular graft system of claim 1 further comprising a second securing rod comprising at least one spike attached to the mating end of the second graft prosthesis such that the at least one spike of the second securing rod is received by the graft material of the mating end of the first graft prosthesis upon conjoining.

12. A securing rod for conjoining endovascular grafts comprising at least one spike jutting from the securing rod against a predetermined dislocation force, wherein the cross-section of the securing rod conforms to the surface of a stent strut.

13. The securing rod of claim 12 wherein the cross-section is part of a circle.

14. The securing rod of claim 12 wherein the at least one spike is laser cut from the securing rod.

15. The securing rod of claim 12 further comprising more than one spike.

\* \* \* \* \*